United States Patent [19]

Malka

[11] Patent Number: 5,453,266
[45] Date of Patent: Sep. 26, 1995

[54] POWDERED BODY DEODORANT COMPOSITION

[76] Inventor: Daniel Malka, 4,Allee de la Quintinie, F-91230 Montgeron, France

[21] Appl. No.: 175,421

[22] PCT Filed: Jul. 6, 1992

[86] PCT No.: PCT/FR92/00640

§ 371 Date: Mar. 7, 1994

§ 102(e) Date: Mar. 7, 1994

[87] PCT Pub. No.: WO93/00885

PCT Pub. Date: Jan. 21, 1993

[30] Foreign Application Priority Data

Jul. 11, 1991 [FR] France ..................... 91 08725

[51] Int. Cl.$^6$ ............ A61K 7/035; A61K 7/36; A61K 7/38
[52] U.S. Cl. ................. 424/65; 424/67; 424/68; 424/698
[58] Field of Search ............... 424/69, 65, 698

[56] References Cited

U.S. PATENT DOCUMENTS

| | | | |
|---|---|---|---|
| 1,813,004 | 7/1931 | Weber | 424/65 |
| 2,145,583 | 1/1939 | Carlson | 424/65 |
| 2,373,933 | 4/1945 | Weeks | 424/69 |
| 2,626,257 | 1/1953 | Caldwell et al. | 424/69 |

FOREIGN PATENT DOCUMENTS

| | | | |
|---|---|---|---|
| 1017506 | 1/1986 | Japan | 424/69 |
| 60317 | 10/1924 | Sweden | 424/69 |
| 16973 | of 1903 | United Kingdom | 424/69 |

OTHER PUBLICATIONS

The Extra Pharmacopoeia, 1941, Martindale, vol. I., pp. 171–172.
Pharmaceutical Formulas, 1946, vol. II., pp. 152, 153, 164–166, and 168 and 177.
Jenkins, 5/44, The Chemistry of Organic Medicinal Products, 2nd Edition.

*Primary Examiner*—Dale R. Ore
*Attorney, Agent, or Firm*—Rodgers & Rodgers

[57] ABSTRACT

A powdered body deodorant composition containing officinal alum, acacia gum, an inert powder and zinc oxide, and intended to be applied twice daily for four days. Said composition reduces excess sweating and prevents foot odour for several years or even permanently.

2 Claims, No Drawings

POWDERED BODY DEODORANT COMPOSITION

This application is a 371 of PCT/FR 92/00640, filed Jul. 6, 1992.

The present invention relates to a powdered body deodorant composition, designed more especially on the basis of pharmaceutical grade alum and gum arabic, for suppressing the growth of bacteria that give rise to disagreeable odors due to excess sweating. This deodorant composition, in the form of a powdered cosmetic, is devised, in particular, so that, following applications to the epidermis, in particular of the feet, repeated twice daily and for approximately four days, the excess sweating is greatly reduced and the disagreeable odors are abolished as a result of the suppression of the formation of bacteria, the effect lasting several years or permanently.

In the prior art, U.S. Pat. No. 2,145,583 is known, which patent describes an anti-odorizing deodorant cream containing aluminum sulfate, water-soluble gum, a zinc salt which is also water-soluble and inert powder, this cream being well tolerated by the skin.

An abstract published in CHEMICAL ABSTRACTS—vol. 115, no. 21 of Nov. 25 1991—is also known, which abstract discloses a deodorant powder containing aluminum-potassium sulfate, this powder being designed to be applied inside shoes.

Although these known products contain alum as an active component, that is to say used for its astringent properties, they do not appear to be applicable for an effective antibacterial treatment but appear, more simply, to be used as a maintenance product for deodorizing sweat.

Consequently, the aim of the present invention is to propose a powdered mixture which complies with the treatment stated in the preamble, and which contains, in equal Amounts in order to supply approximately 65 to 75% of its total amount, pharmaceutical grade alum in the form of aluminum potassium sulfate and gum arabic extracted from acacia, as well as an amount of zinc oxide of approximately 5 to 10%, and the remaining amount of inert powder consisting of talc and forming approximately 20 to 25% of this mixture.

It should be noted that these components, apart from pharmaceutical grade alum which has long been known for its astringent properties, were chosen to enhance the effects of the latter product, that is to say, gum arabic has the effect of maintaining the closing of the pores caused by alum and, at the same time, of constituting a demulcent for the epidermis, zinc oxide speeds up desiccation and talc, as a result of being insoluble in water, yields an inert powder which is non-fermentable.

After different mixtures of powders were made, but in proportions lying within the percentage ranges stated previously, and after they were used on a trial basis on patients suffering from excess sweating and who developed disagreeable odors even though they regularly complied with attention to body hygiene, mycobacteriological examinations were carried out on sweat samples and, following the results, the inventor noted that the most satisfactory powdered mixture was that specifically containing the following amounts: 35% of pharmaceutical grade alum, 35% of gum arabic, 5% of zinc oxide and 25% of talc.

Following this, the inventor has discontinued his trials, and believes that his new deodorant composition is appropriately suited to the treatment he envisages for abolishing excess body sweating, and of the feet in particular, for several years.

I claim:

1. A body deodorant composition in powder form, which can be applied to the epidermis, in particular to the epidermis of the feet and contains a large quantity of alum as astringent, relative to a small quantity of zinc oxide as desiccation accelerator, which composition incorporates, in a quantity equal to that of the alum, gum arabic extracted from acacia, as a product for maintaining the effect of closing of the pores brought about by the alum, which is in the form of a double sulfate of aluminum and potassium, which constitutes with the gum arabic a quantity of from approximately 65% to 75% of the total quantity of the composition, and which incorporates a quantity of from approximately 5% to 10% of zinc oxide, the remaining quantity up to 100% consisting of inert, nonfermentable powder.

2. A body deodorant composition in powder form as claimed in claim 1, which incorporates a quantity of 35% of double sulfate of aluminum and potassium and an equal quantity of gum arabic a quantity of 5% of zinc oxide, the remaining quantity of 25% consisting of talc.

* * * * *